United States Patent
Henmi et al.

(10) Patent No.: US 11,432,552 B2
(45) Date of Patent: Sep. 6, 2022

(54) DEODORIZING/ANTIBACTERIAL AGENT

(71) Applicants: RILIS CO., LTD., Osaka (JP); KINKI UNIVERSITY, Higashiosaka (JP)

(72) Inventors: Atsushi Henmi, Osaka (JP); Masato Nomura, Higashihiroshima (JP)

(73) Assignees: RILIS CO., LTD., Osaka (JP); KINKI UNIVERSITY, Osaka (JP)

(*) Notice: Subject to any disclaimer, the term of this patent is extended or adjusted under 35 U.S.C. 154(b) by 10 days.

(21) Appl. No.: 16/491,956

(22) PCT Filed: Mar. 2, 2018

(86) PCT No.: PCT/JP2018/008046
§ 371 (c)(1),
(2) Date: Sep. 6, 2019

(87) PCT Pub. No.: WO2018/163996
PCT Pub. Date: Sep. 13, 2018

(65) Prior Publication Data
US 2021/0127687 A1 May 6, 2021

(30) Foreign Application Priority Data
Mar. 7, 2017 (JP) .............................. JP2017-043030

(51) Int. Cl.
*A01N 65/34* (2009.01)
*A61K 36/73* (2006.01)
*A61L 9/013* (2006.01)
*A01N 35/04* (2006.01)
*A01N 65/08* (2009.01)
*A01N 65/00* (2009.01)
*A01N 37/10* (2006.01)
*A61L 9/01* (2006.01)
*A61L 101/36* (2006.01)

(52) U.S. Cl.
CPC ............ *A01N 65/34* (2013.01); *A01N 35/04* (2013.01); *A01N 37/10* (2013.01); *A01N 65/08* (2013.01); *A61L 9/01* (2013.01); *A61L 9/013* (2013.01); *A61L 2101/36* (2020.08)

(58) Field of Classification Search
None
See application file for complete search history.

(56) References Cited

U.S. PATENT DOCUMENTS

2001/0028899 A1* 10/2001 Nishioka ................ A61P 11/00
424/776

FOREIGN PATENT DOCUMENTS

| CN | 101040880 A | 9/2007 | |
|---|---|---|---|
| JP | H10-108691 A | 4/1998 | |
| JP | 2003-246745 A | 9/2003 | |
| JP | H10-108691 A5 | 10/2004 | |
| JP | 2006-304761 A | 11/2006 | |
| JP | 2008-289992 A | 12/2008 | |
| WO | WO-03070022 A1 * | 8/2003 | ............... A23L 2/52 |

OTHER PUBLICATIONS

Li, Ke, et al. "Extraction and characterization of oil from Mudong bayberry (Myrica rubra) kernels." Emirates Journal of Food and Agriculture (2016): 689-694. (Year: 2016).*
Yokota, Junko, et al. "Scavenging of reactive oxygen species by Eriobotrya japonica seed extract." Biological and Pharmaceutical Bulletin 29.3 (2006): 467-471. (Year: 2006).*
Cheng, Jiyu, et al. "Nutritional composition of underutilized bayberry (Myrica rubra Sieb. et Zucc.) kernels." Food chemistry 107.4 (2008): 1674-1680. (Year: 2008).*
Minori Shoji et al., "Oil Composition of Loquat (Eriobotrya japonica (Thumb.) Lindl.) Seed and its Utilization", Abstracts, The 55th Annual Meeting of the Japan Oil Chemists' Society, Nara Women's University, dated Sep. 7-9, 2016, 3 pages.
Atsushi Ogimi, et al., *Deodorant and antibacterial effects of loquat and bayberry seed oil (short report)*, 46 J. Japan Soc'y Anti-Bacteria & Anti-Mold 349 (2018).

* cited by examiner

Primary Examiner — Bethany P Barham
Assistant Examiner — Peter Anthopolos
(74) Attorney, Agent, or Firm — Crowell & Moring LLP

(57) ABSTRACT

To improve the fact that the main components of conventional deodorizing and antimicrobial agents are existing components, the effect and efficacy of which are known to some extent, and do not generate an effect better than predicted. The deodorizing and antimicrobial agent of the present invention has a loquat seed extract including non-volatile fatty acids and at least benzaldehyde and benzoic acid as a main raw material.

5 Claims, 2 Drawing Sheets

| Malodorous components | Malodor concentration (ppm) | Loquat seed extract | Mixture of loquat and bayberry seed extracts (1:1) | Mixture of loquat and bayberry seed extracts (1:3) |
|---|---|---|---|---|
| Ammonia | 150 | 99.9 | 99.9 | 99.9 |
| Trimethylamine | 20 | 99.9 | 99.9 | 99.9 |
| Acetic acid | 50 | 20.0 | 55.0 | 72.0 |
| Isovaleric acid | 50 | 95.4 | 98.4 | 98.4 |
| 2-Nonenal | 10 | 94.5 | 98.0 | 99.0 |
| Hydrogen sulfide | 20 | 90.0 | 95.0 | 95.0 |
| Methyl mercaptan | 5 | 33.0 | 50.0 | 60.0 |
| Allyl mercaptan | 1 | 61.4 | 80.0 | 85.0 |
| Allyl methyl sulfide | 1 | 67.3 | 76.0 | 82.0 |
| Dimethyl disulfide | 1 | 66.0 | 67.0 | 72.0 |
| Dimethyl trisulfide | 1 | 91.0 | 93.0 | 96.0 |

Fig. 3

|  | Escherichia coli Inhibition ring (mm) | Bacillus subtilis Inhibition ring (mm) |
|---|---|---|
| No samples added | ----- | ----- |
| Loquat seed extract | 0.5 | ----- |
| Mixture of loquat and bayberry seed extracts (1:1) | 0.5 | ----- |
| Mixture of loquat and bayberry seed extracts (1:3) | 1.0 | 0.5 |
| Mixture of loquat and bayberry seed extracts (1:5) | 2.5 | 2.0 |

DEODORIZING/ANTIBACTERIAL AGENT

This application is a 371 application of PCT/W2018/008046 having an international filing date of Mar. 2, 2018, which claims priority to JP2017-43030 filed Mar. 7, 2017, the entire content of each of which is incorporated herein by reference.

TECHNICAL FIELD

The present invention relates to a deodorizing and antimicrobial agent, which removes several malodorous components simultaneously and also has an antimicrobial effect, and moreover is relatively safe even when used in living environments.

BACKGROUND ART

There are various malodorous components in living spaces. In living spaces, meanwhile, there exist a large number of microbes which have a bad influence on, for example, human bodies, and which themselves have a less influence on human bodies but decay, e.g. food. Conventionally, there are Patent Literatures 1 to 4 as techniques which can obtain deodorizing and antimicrobial effects simultaneously.

In order to provide an antimicrobial deodorizing cleaning composition, having the power of decomposing organic matters by the antimicrobial action and enzyme action on various microbes causing malodor and sliminess which have acquired resistance in, e.g. drainage routes, and also having high safety for human and environments, Patent Literature 1 is characterized by being obtained by combining a cationic polymer using naturally occurring chitosan having a potent antimicrobial activity, and a microorganism material which is not affected by the antimicrobial activity of chitosan and uses *Bacillus subtilis* genus or *Lactobacillus* genus microorganism having the excellent properties of decomposing organic matters.

In order to provide a cleaning liquid for pet excrement which has deodorizing and cleaning effects and does not damage the environment, Patent Literature 2 is characterized by including a naturally occurring antimicrobial compound which has water as a base material and has an antimicrobial action, a naturally occurring neutralizing compound which has a neutralizing action on alkali values, a naturally occurring deodorizing compound which has a deodorizing action, and a naturally occurring growth promoting compound which promotes plant growth.

In order to provide a fragrance and cosmetic material which when applied to skin and hair shows, e.g., an antimicrobial action and a deodorizing action leading to maintaining and improving physiology, prevents aging, atrophy and variation, and also prevents and cures disorders and lesions to maintain health, Patent Literature 3 is characterized by mixing amygdalin or a plant extract liquid or extract including amygdalin of apricot kernels, peach kernels, loquat seeds or Japanese plum seeds.

In order to provide a hot pack which can be warmed in a short time, emits far infrared rays promoting blood flow, and also has an antimicrobial action and an odor removing and deodorizing action, Patent Literature 4 is characterized by filling a mixture including one or two types of corn or soybean and loquat leaves in a bag formed from a fabric including tourmaline.

However, main components such as a cationic polymer using naturally occurring chitosan, and a microorganism material using *Bacillus subtilis* genus or *Lactobacillus* genus microorganism in Patent Literature 1, a naturally occurring antimicrobial compound which has an antimicrobial action, and a naturally occurring deodorizing compound which has a deodorizing action in Patent Literature 2, amygdalin or plant including amygdalin of apricot kernels, peach kernels, loquat seeds or Japanese plum seeds in Patent Literature 3, and one or two types of corn or soybean and loquat leaves in Patent Literature 4, are existing components, the effect and efficacy of which are known to some extent, and a certain effect predicted has been recognized; however, an effect better than predicted has not been generated.

CITATION LIST

Patent Literature

Patent Literature 1: Japanese Unexamined Patent Application Publication No. 2012-232905
Patent Literature 2: Japanese Unexamined Patent Application Publication No. 2012-167043
Patent Literature 3: Japanese Unexamined Patent Application Publication No. 2005-187474
Patent Literature 4: Japanese Unexamined Patent Application Publication No. 2000-217855

SUMMARY OF INVENTION

Technical Problem

A problem to be solved is that main components conventionally are existing components, the effect and efficacy of which are known to some extent, and a certain effect predicted is recognized, but an effect better than predicted is not generated.

Solution To Problem

In order to solve the above problem, the deodorizing and antimicrobial agent of the present invention is characterized by having a loquat seed extract including non-volatile fatty acids and at least benzaldehyde and benzoic acid as a main raw material.

Advantageous Effect of Invention

According to the above constitution, it was observed that loquat itself is an existing plant; however, by investigating this loquat, in an extract of not sites such as loquat leaves and branches but seeds, loquat seed extract, non-volatile fatty acids and at least benzaldehyde and benzoic acid were combined to show an antimicrobial and deodorizing effect. That is, when using a mere loquat seed extract, the effect and efficacy are within a range which can be predicted as described above; however, by a loquat seed extract including non-volatile fatty acids and at least benzaldehyde and benzoic acid, an antimicrobial and deodorizing effect better than the one obtained when using a mere loquat seed extract, which has been conventionally used, can be obtained.

BRIEF DESCRIPTION OF DRAWING

FIG. 3 is a table which shows the results of experiments about the antimicrobial effect of the present invention.

DESCRIPTION OF EMBODIMENT

Figures 1, 2:
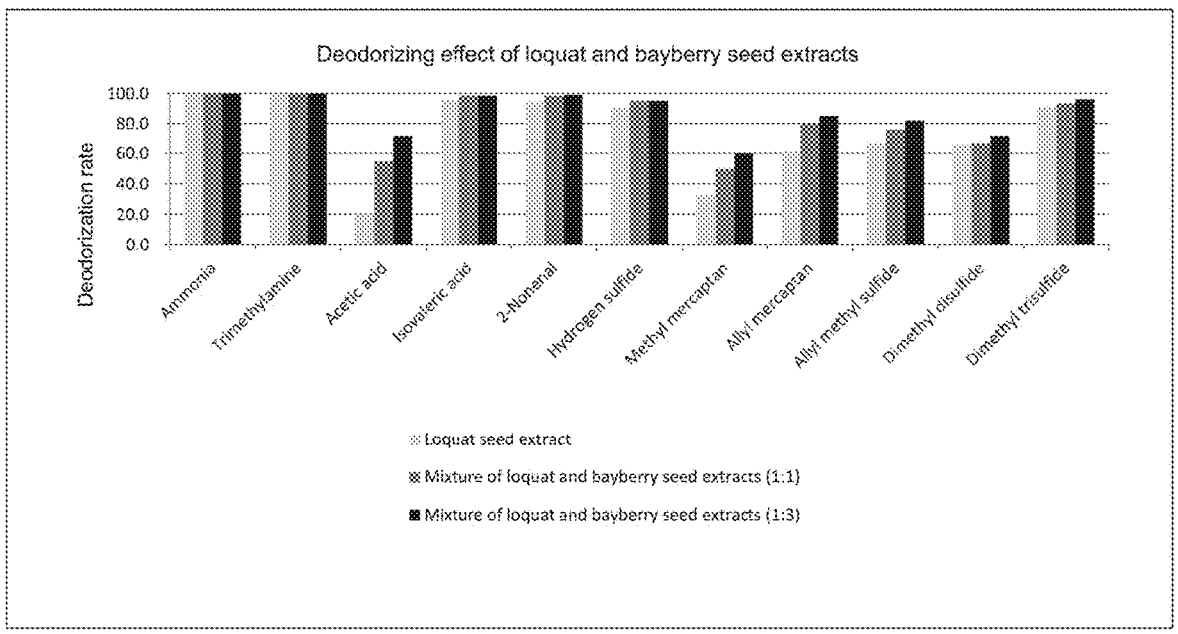
FIG. 1 is a table which shows the results of experiments about the deodorizing effect of the present invention.
FIG. 2 is a graph which summarizes the table in FIG. 1 of the present invention.

Even though a main component is an existing component, the effect and efficacy of which are known to some extent, and a certain effect predicted is recognized, the inventors of this application and the like diligently and repeatedly investigated to obtain an effect better than predicted, and consequently reached the invention of this application by the following knowledge.

That is, a loquat seed extract including non-volatile fatty acids and at least benzaldehyde and benzoic acid is not obtained by a conventional technique such as alkaline extraction, which is generally carried out to extract a component such as polyphenol (an extract obtained by such technique is described as the above "mere" in this application), and is obtained by a technique for extraction of oil components. As a specific example, loquat seeds are pulverized, and immersed in hexane at room temperature for about 10 days, and the obtained mixture is filtered, followed by distilling hexane.

In the case of loquat seeds, by the above technique for extraction of oil components, particularly palmitic acid, linoleic acid, behenic acid and lignoceric acid are extracted as the non-volatile fatty acids, and benzaldehyde, benzoic acid and methyl benzoate are extracted in addition to these non-volatile fatty acids. These are combined to obtain an effect better than predicted.

In the present invention, a bayberry seed extract including non-volatile fatty acids may be added in the above. It was observed by the inventors of this application and the like that by adding a bayberry seed extract including non-volatile fatty acids to a loquat seed extract including non-volatile fatty acids and at least benzaldehyde and benzoic acid, which shows an effect better than the one obtained when using a mere loquat seed extract, the effects of the loquat seed extract including non-volatile fatty acids and at least benzaldehyde and benzoic acid and the bayberry seed extract including non-volatile fatty acids were not inhibited by each other, points with a low effect of both were complemented, and also a synergetic effect was expressed.

It was further observed by the inventors of this application and the like that when a bayberry seed extract including non-volatile fatty acids is added to the above loquat seed extract including non-volatile fatty acids and at least benzaldehyde and benzoic acid, complementary and synergetic effects became further remarkable by setting the mixing ratio of both to 1:3 to 1:5.

In a case where a loquat seed extract including non-volatile fatty acids and at least benzaldehyde and benzoic acid is considered as 1, when the mixing ratio of a bayberry seed extract including non-volatile fatty acids is lower than 3, the complementary and synergetic effects of the bayberry seed extract including non-volatile fatty acids on the deodorizing and antimicrobial effect of the loquat seed extract including non-volatile fatty acids and at least benzaldehyde and benzoic acid are low. Even when the mixing ratio of the bayberry seed extract including non-volatile fatty acids is higher than 5, the complementary and synergetic effects on the deodorizing and antimicrobial effect of the loquat seed extract including non-volatile fatty acids and at least benzaldehyde and benzoic acid cannot be expected to be higher, leading to waste.

EXAMPLES

Seed Extract

A loquat seed extract including non-volatile fatty acids and at least benzaldehyde and benzoic acid, and a bayberry extract including non-volatile fatty acids were obtained by pulverizing each seed, immersing the obtained pulverized seeds in hexane at room temperature for about 10 days, filtering the obtained mixture and distilling hexane. The loquat seed extract including non-volatile fatty acids and at least benzaldehyde and benzoic acid, and the bayberry extract including non-volatile fatty acids will now be referred to as "loquat seed extract" and "bayberry seed extract" respectively.

It was found that by the above extraction, oil components were included at about 43% in the loquat seed extract, among these many of non-volatile fatty acids were behenic acid and lignoceric acid as described above, and benzaldehyde, methyl benzoate and benzoic acid were largely included in other components extracted at about 57%. Meanwhile, it was found that about 97% of bayberry seed extract was oil components, and among these particularly linoleic acid and oleic acid were largely included as the non-volatile fatty acids.

Method for Testing Deodorizing Effect

1: To a 300 ml glass conical flask, 50 mg of loquat seed extract, 50 mg of bayberry seed extract or 50 mg each of both extracts were added to prepare a sample flask. In addition, a blank flask without a sample was prepared as a blank.

2: The following malodorous solution was added thereto, and a flask was immediately sealed and left to stand for an hour.

(Malodorous components) ammonia, trimethylamine, acetic acid, isovaleric acid, 2-nonenal, hydrogen sulfide, methyl mercaptan, allyl mercaptan, allyl methyl sulfide, dimethyl disulfide, and dimethyl trisulfide.

3: The malodor in the head space section was measured using a gas detector tube or gas chromatograph.

It should be noted that ammonia, trimethylamine, acetic acid, isovaleric acid, hydrogen sulfide and methyl mercaptan were measured by the "gas detector tube", and 2-nonenal, allyl mercaptan, allyl methyl sulfide, dimethyl disulfide and dimethyl trisulfide by the "gas chromatograph."

4: The deodorization rate to each malodor was calculated by the following formula. It should be noted that BK in the following formula means blank.

Deodorization Rate %={(measurement value of BK flask−measurement value of sample flask)/measurement value of BK flask}×100PS Results of Deodorizing Effect According to FIG. 1 and FIG. 2, the experiment results of the deodorizing effect were as follows. When using only the loquat seed extract, the deodorization rates to ammonia, trimethylamine, isovaleric acid, 2-nonenal, hydrogen sulfide and dimethyl trisulfide were 90% or more (odorless in a sensory test). In addition, when using only the loquat seed extract, the deodorization rates to allyl mercaptan, allyl methyl sulfide and dimethyl disulfide were 60% or more (almost odorless in a sensory test).

In addition, when to the loquat seed extract the bayberry extract was added in a ratio of 1:1, the deodorization rates to all malodorous components were improved. It should be noted that when using only the loquat seed extract, the deodorization rates to ammonia and trimethylamine were 99.9%, and this value was not reduced. It is notable that when using only the loquat seed extract, the deodorization rate to acetic acid was 20.0% and the deodorization rate to methyl mercaptan was 33.0%; however, when adding the bayberry seed extract, the deodorization rates were 55.0% and 50.0%, which were improved to a degree in which the deodorizing effect can be felt in a sensory test.

Furthermore, when to the loquat seed extract the bayberry extract was added in a ratio of 1:3, the deodorization rates to all malodorous components were 60.0% or more, which were improved to an almost odorless level in a sensory test. It is notable that when to the loquat seed extract the bayberry extract was added, the deodorizing effect on the malodorous components, on which the loquat seed extract originally has a high deodorizing effect, is not reduced, and when the ratio of the bayberry extract is increased, the deodorizing effect on the malodorous components, on which the deodorizing effect obtained by using only the loquat seed extract is low, is complementarily and synergistically improved.

It should be noted that when to the loquat seed extract the bayberry extract was added in a ratio of 1:5, the deodorization rates to all malodorous components were 90.0% or more, which were improved to an odorless level in a sensory test, and thus the results in the case of a ratio of 1:5 and the results in the case of a ratio of 1:5 or more were omitted.

Method for Testing Antimicrobial Effect

The antimicrobial effect was verified by Halo method.
1: To $1\times10^7$ CFU/ml *Escherichia coli* and 1 ml *Bacillus subtilis*, 15 ml of agar medium was added to produce a pour medium.
2: A sample was put on a paper disk medium in each designated addition amount.
3: After culturing at 37° C. for 24 hours, a growth inhibition ring (width) was measured.

Test Samples

Loquat seed extract 5 mg (1:0)
Loquat seed extract 5 mg+bayberry seed extract 5 mg (1:1)
Loquat seed extract 5 mg+bayberry seed extract 15 mg (1:3)
Loquat seed extract 5 mg+bayberry seed extract 25 mg (1:5)

Results of Antimicrobial Effect

According to FIG. 3, the results of experiments about the antimicrobial effect were as follows. When using only the loquat seed extract (1:0), the inhibition ring of *Escherichia coli* was 0.5 mm, and the antimicrobial effect could be verified. When using the loquat seed extract and the bayberry seed extract at 1:1, the inhibition ring of *Escherichia coli* was also 0.5 mm. It is notable that even when the loquat seed extract was diluted with the bayberry seed extract, the inhibition ring of *Escherichia coli* did not become small. Because of this, adding the bayberry seed extract is not a disadvantage for the whole effect including the above deodorizing effect.

In addition, it could be verified that when the ratio of the loquat seed extract and the bayberry seed extract is 1:3, the inhibition ring of *Escherichia coli* was enlarged to 1.0 mm, and also the inhibition ring of *Bacillus subtilis* was 0.5 mm. It could be further verified that when the ratio of the loquat seed extract and the bayberry seed extract is 1:5, the inhibition ring of *Escherichia coli* was enlarged to 2.5 mm, and also the inhibition ring of *Bacillus subtilis* was enlarged to 2.0 mm.

Because of this, the antimicrobial effect could be also verified using only the loquat seed extract, and when adding the bayberry seed extract to the loquat seed extract, the complementary and synergetic effects could be verified without inhibiting the effect of the loquat seed extract.

Industrial Applicability

Loquat and bayberry grow naturally even in soil with low nutritional values and can be relatively easily grown. Therefore, costs for raw materials as a deodorizing and antimicrobial agent can be kept low. Because the deodorizing and antimicrobial agent of the present invention includes only a loquat seed extract and a bayberry seed extract, that is, only naturally occurring components, it is relatively safe in uses in living spaces, for example when it is drunk by mistake and aspirated when sprayed. Therefore, it can be positively used not only in general households but also various places such as hospitals, nursing homes, infant care facility and restaurants.

1. Malodorous components
2. Malodor concentration
3. Loquat seed extract
4. Mixture of loquat and bayberry seed extracts
5. Ammonia
6. Trimethylamine
7. Acetic acid
8. Isovaleric acid
9. 2-Nonenal
10. Hydrogen sulfide
11. Methyl mercaptan
12. Allyl mercaptan
13. Allyl methyl sulfide
14. Dimethyl disulfide
15. Dimethyl trisulfide
16. Deodorizing effect of loquat and bayberry seed extracts
17. Deodorization rate
18. *Escherichia coli*
19. *Bacillus subtilis*
20. Inhibition ring
21. No samples added

What is claimed is:
1. A deodorizing and antimicrobial agent, comprising:
a loquat seed extract comprising non-volatile fatty acids and at least benzaldehyde and benzoic acid;
a bayberry seed extract comprising non-volatile fatty acids;
wherein a mass:mass ratio of the loquat seed extract to the bayberry seed extract is from 1:3 to 1:5.
2. The deodorizing and antimicrobial agent according to claim 1, wherein the agent is topical.
3. The deodorizing and antimicrobial agent according to claim 1, wherein the agent synergistically inhibits *Escherichia coli* and *Bacillus subtilis* more than the loquat seed extract individually.
4. The deodorizing and antimicrobial agent according to claim 1, wherein the non-volatile fatty acids comprise one or more fatty acids selected from the group consisting of palmitic acid, linoleic acid, behemic acid, oleic acid, and lignoceric acid.

5. A method of preparing the deodorizing and antimicrobial agent according to claim 1, comprising:
  extracting from loquat seeds, with hexane, a loquat seed extract comprising palmitic acid, linoleic acid, behemic acid, lignoceric acid, benzaldehyde, and benzoic acid;
  extracting from bayberry seeds, with hexane, a bayberry seed extract comprising linoleic acid and oleic acid; and
  mixing the loquat seed extract and the bayberry seed extract so as to produce the deodorizing and antimicrobial agent;
  wherein the mass:mass ratio of the mixing of the loquat seed extract to the bayberry seed extract is from 1:3 to 1:5.

* * * * *